(12) United States Patent
Greenberg et al.

(10) Patent No.: US 8,864,808 B2
(45) Date of Patent: Oct. 21, 2014

(54) ENDOLUMINAL DELIVERY ASSEMBLY

(75) Inventors: Roy K. Greenberg, Bratenahl, OH (US); David Ernest Hartley, Subiaco (AU)

(73) Assignees: The Cleveland Clinic Foundation, Cleveland, OH (US); Cook Medical Technologies LLC, Bloomington, IN (US)

( * ) Notice: Subject to any disclaimer, the term of this patent is extended or adjusted under 35 U.S.C. 154(b) by 1891 days.

(21) Appl. No.: 11/524,855

(22) Filed: Sep. 21, 2006

(65) Prior Publication Data

US 2007/0088424 A1    Apr. 19, 2007

Related U.S. Application Data

(60) Provisional application No. 60/719,081, filed on Sep. 21, 2005.

(51) Int. Cl.
| A61F 2/06 | (2013.01) |
| A61F 2/954 | (2013.01) |
| A61F 2/966 | (2013.01) |
| A61F 2/95 | (2013.01) |
| A61F 2/07 | (2013.01) |
| A61M 25/01 | (2006.01) |

(52) U.S. Cl.
CPC .......... *A61F 2/954* (2013.01); *A61F 2002/9665* (2013.01); *A61F 2002/061* (2013.01); *A61F 2002/9505* (2013.01); *A61F 2002/9517* (2013.01); *A61F 2002/9511* (2013.01); *A61F 2/07* (2013.01); *A61M 25/0152* (2013.01)
USPC ........................................................ 623/1.11

(58) Field of Classification Search
CPC .................................. A61F 2/95–2/97; A61F 2002/9505–2002/9665
USPC .............. 623/1.11, 1.13, 1.24, 1.23; 606/108, 606/113, 191–195, 198; 604/103.04, 604/103.05, 103.08
See application file for complete search history.

(56) References Cited

U.S. PATENT DOCUMENTS

| 5,405,378 | A | * | 4/1995 | Strecker | 623/1.12 |
| 5,509,902 | A | * | 4/1996 | Raulerson | 604/175 |
| 5,873,906 | A | * | 2/1999 | Lau et al. | 128/898 |
| 6,302,891 | B1 | * | 10/2001 | Nadal | 606/108 |
| 6,352,561 | B1 | * | 3/2002 | Leopold et al. | 623/1.23 |
| 6,371,979 | B1 | * | 4/2002 | Beyar et al. | 623/1.12 |

(Continued)

FOREIGN PATENT DOCUMENTS

| EP | 0664107 | 7/1995 |
| WO | 0334948 | 5/2003 |
| WO | 0417868 | 3/2004 |

OTHER PUBLICATIONS

International Search Report Issued for Application Serial No. PCT/US2006/036895.

*Primary Examiner* — Darwin Erezo
*Assistant Examiner* — Jonathan Hollm
(74) *Attorney, Agent, or Firm* — Brinks Gilson & Lione (57) ABSTRACT

A stent graft delivery system in which a stent graft (6) is retained on a delivery device (2) such that a longitudinal portion of the stent graft is releasably retained on the delivery device to bend therewith. The delivery device (2) has a guide wire catheter (3) and the stent graft is retained onto the guide wire catheter by a release wire (24) which can be withdrawn. The release wire is wound around the guide wire catheter and through the stent graft or suture loops engage around the guide wire catheter and release wire.

19 Claims, 7 Drawing Sheets

(56) References Cited

U.S. PATENT DOCUMENTS

| | | | |
|---|---|---|---|
| 6,607,539 B1 * | 8/2003 | Hayashi et al. | 606/108 |
| 6,648,911 B1 * | 11/2003 | Sirhan et al. | 623/1.15 |
| 7,101,390 B2 * | 9/2006 | Nelson | 623/1.12 |
| 2004/0106974 A1 * | 6/2004 | Greenberg et al. | 623/1.11 |
| 2004/0243215 A1 * | 12/2004 | Nelson | 623/1.12 |
| 2006/0014836 A1 * | 1/2006 | Chen et al. | 514/584 |

* cited by examiner

ENDOLUMINAL DELIVERY ASSEMBLY

CROSS-REFERENCE TO RELATED APPLICATIONS

This application claims priority of provisional application Ser. No. 60/719,081, filed Sep. 21, 2005.

TECHNICAL FIELD

This invention relates to a delivery device or deployment device for intraluminal or endovascular delivery of a stent graft.

BACKGROUND OF THE INVENTION

The invention will be discussed generally with respect to deployment of a stent graft into the thoracic aorta but is not so limited and may apply to deployment into other body lumens.

It is important when delivering a stent graft by intraluminal or endovascular methods to know exactly where the device is in the vasculature particularly in relation to branch vessels which could be adversely occluded by placement of the stent graft. To avoid occlusion there have been proposed fenestrations along the length of a stent graft and scalloping at the proximal and distal ends of the stent graft to allow flow from a main vessel to a branch vessel through the fenestration or scallop.

The use of radiopaque markers around the periphery of the fenestration or scallop in this regard has been proposed but it would be advantageous if a more certain or reliable method could be devised to assist with placement.

Particularly when deploying into a curved vessel it is known that a deployment device will take up a position in the vessel on the outside or greater radius side of the curved vessel and hence if a stent graft could be retained onto a deployment device so that a fenestration or scallop on the stent graft is in a selected position with respect to a portion of the deployment device when it is curved then more accurate positioning may be possible.

As a particular example, the aorta of a patient comprises an ascending aorta from the aortic heart valve, a thoracic arch and a descending aorta. Major branch vessels extend from the thoracic arch and occlusion of one or more of these upon placement of a stent graft in the thoracic arch could have serious consequences. The major vessels generally extend from the outside or greater radius side of the curved thoracic arch and so if a was stent graft retained onto a deployment device such that a scallop on the stent graft was on the outside of the deployment device when it is curved then correct placement would be surer.

It is known to retain the proximal and distal ends of a stent graft onto a deployment device to facilitate relative longitudinal and rotational movement of the ends but owing to tortuosity of vessels through which a deployment device must be progressed and the rotation necessity to achieve progression the final rotational position of a stent graft may not be fully known.

It is an object of this invention to provide a retention mechanism for a stent graft onto a deployment device for more accurate deployment of the stent graft therefrom or to at least provide a practitioner with a useful alternative.

Throughout this specification the term distal with respect to a portion of the aorta, a deployment device or a stent graft is intended to mean the portion of the aorta, deployment device or stent graft further away in the direction of blood flow away from the heart and the term proximal is intended to mean the portion of the aorta, deployment device or end of the stent graft nearer to the heart. When applied to other vessels similar terms such as caudal and cranial should be understood.

SUMMARY OF THE INVENTION

In one form the invention is said to reside in an endovascular delivery device and a stent graft mounted thereon;
the delivery device comprising a pusher catheter and a distal handle,
a proximal nose cone dilator,
a guide wire catheter extending from the pusher catheter to and through the nose cone dilator,
the stent graft comprising a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and the guide wire catheter passing through the lumen of the stent graft;
characterised by the stent graft being releasably fastened to the guide wire catheter along at least part of the length of the stent graft whereby the stent graft curves with curvature of the guide wire catheter in use.

Preferably the pusher catheter comprises a longitudinal lumen therethrough, the guide wire catheter extending through the longitudinal lumen so that the guide wire catheter is movable longitudinally and rotationally with respect to the pusher catheter.

There may be further included a flexible sheath over the pusher catheter and extending to the nose cone dilator and thereby retaining the stent graft in a contracted conformation on the guide wire catheter.

The releasable fastening can comprise a release wire system to releasably retain the stent graft to the guide wire catheter.

The release wire system to releasably retain the stent graft to the guide wire catheter can comprise a wire wound around the guide wire catheter and through the material of the stent graft in a spiral manner, the wire extending to the distal handle. The pitch of the spiral wound wire can be between 20 to 40 mm.

Alternatively there can be a plurality of suture loops fastened to the stent graft tubular body and around the guide wire catheter and looped around the release wire whereby when the release wire is withdrawn the suture loops are released to release the stent graft from the guide wire catheter. The release wire may be stitched or looped in and out of the material of the stent graft along the length of the stent graft.

There can further be a releasable retention system for a proximal end of the stent graft and a releasable retention system for a distal end of the stent graft.

The guide wire catheter can have a pre-formed curve just distal of the nose cone dilator to assist with the deployment device fitting into the thoracic arch. The flexible sheath can also have a pre-formed curve at its proximal end again to assist with the deployment device fitting into the thoracic arch.

In a further form the invention is said to reside in a stent graft delivery system in which a stent graft is retained on the delivery system such that a longitudinal portion of the stent graft is releasably retained on the delivery device to bend therewith.

In a further form the invention is said to reside in an endovascular delivery device and a stent graft mounted thereon;

the delivery device comprising a pusher catheter, a distal handle on the pusher catheter, a proximal nose cone dilator, a guide wire catheter extending from the pusher catheter to and through the nose cone dilator and a flexible sheath over the pusher catheter and extending to the nose cone dilator and thereby retaining the stent graft in a contracted conformation on the guide wire catheter.

the stent graft comprising a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and the guide wire catheter passing through the lumen of the stent graft;

a release wire system to releasably retain the stent graft to the guide wire catheter, the release wire system including a release wire wound around the guide wire catheter and through the material of the stent graft in a spiral manner along at least part of the length of the stent graft and the release wire extending to a release mechanism on the distal handle to enable withdrawal of the release wire whereby the stent graft is temporarily affixed to the guide wire catheter and curves with curvature of the guide wire catheter in use and whereby when the release wire is withdrawn the stent graft is released from the guide wire catheter.

In a further form the invention is said to reside in an endovascular delivery device and a stent graft mounted thereon;

the delivery device comprising a pusher catheter, a distal handle on the pusher catheter, a proximal nose cone dilator, a guide wire catheter extending from the pusher catheter to and through the nose cone dilator and a flexible sheath over the pusher catheter and extending to the nose cone dilator and thereby retaining the stent graft in a contracted conformation on the guide wire catheter.

the stent graft comprising a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and the guide wire catheter passing through the lumen of the stent graft;

a release wire system to releasably retain the stent graft to the guide wire catheter, the release wire system including a release wire stitched along at least part of the length of the stent graft and a plurality of suture loops fastened to the tubular body of the stent graft and looped around the guide wire catheter and the stitches of the release wire and the release wire extending to a release mechanism on the distal handle to enable withdrawal of the release wire whereby the stent graft is temporarily affixed to the guide wire catheter and curves with curvature of the guide wire catheter in use and whereby when the release wire is withdrawn the stent graft is released from the guide wire catheter.

This then generally describes the invention but to assist with understanding reference will now be made to preferred embodiments of the invention.

DETAILED DESCRIPTION

FIGS. 1, 2 and 3A and 3B depict a delivery device 2 according to one embodiment of the invention. The delivery device 2 has a guide wire catheter 3 which extends from a distal handle 7 to a proximal tapered nose cone dilator 11 longitudinally through a passageway or lumen 5 of a delivery catheter 4 which is connected to the handle 7 at its distal end. An introducer sheath 10 fits coaxially around the delivery catheter 4 and extends from a tapered proximal end 13 which optionally includes a radiopaque marker to a connector valve and manipulator 14 attached about distal end 15 of the sheath. The introducer sheath 10 extends proximally to the nose cone dilator 11 and covers the stent graft 6 during introduction of the deployment device into a patient and is withdrawn distally to expose the stent graft 6 during deployment when the deployment device is in a selected position within the vasculature of a patient. The stent graft or implantable device 6 is carried on the guide wire catheter 3 proximally of the delivery catheter 4 and distally of the nose cone dilator 11. Connector valve 14 includes a silicone disk (not shown) for preventing the backflow of fluids therethrough. The disk includes a slit for the insertion of the nose cone dilator 11 and delivery catheter 4. Connector 14 also includes side arm 16 to which a tube 17 is connected for introducing and aspirating fluids therethrough. Nose cone dilator 11 includes a tapered proximal end 19 for accessing and dilating a vascular access site over a well-known and commercially available wire guide (not shown).

Figure 1:
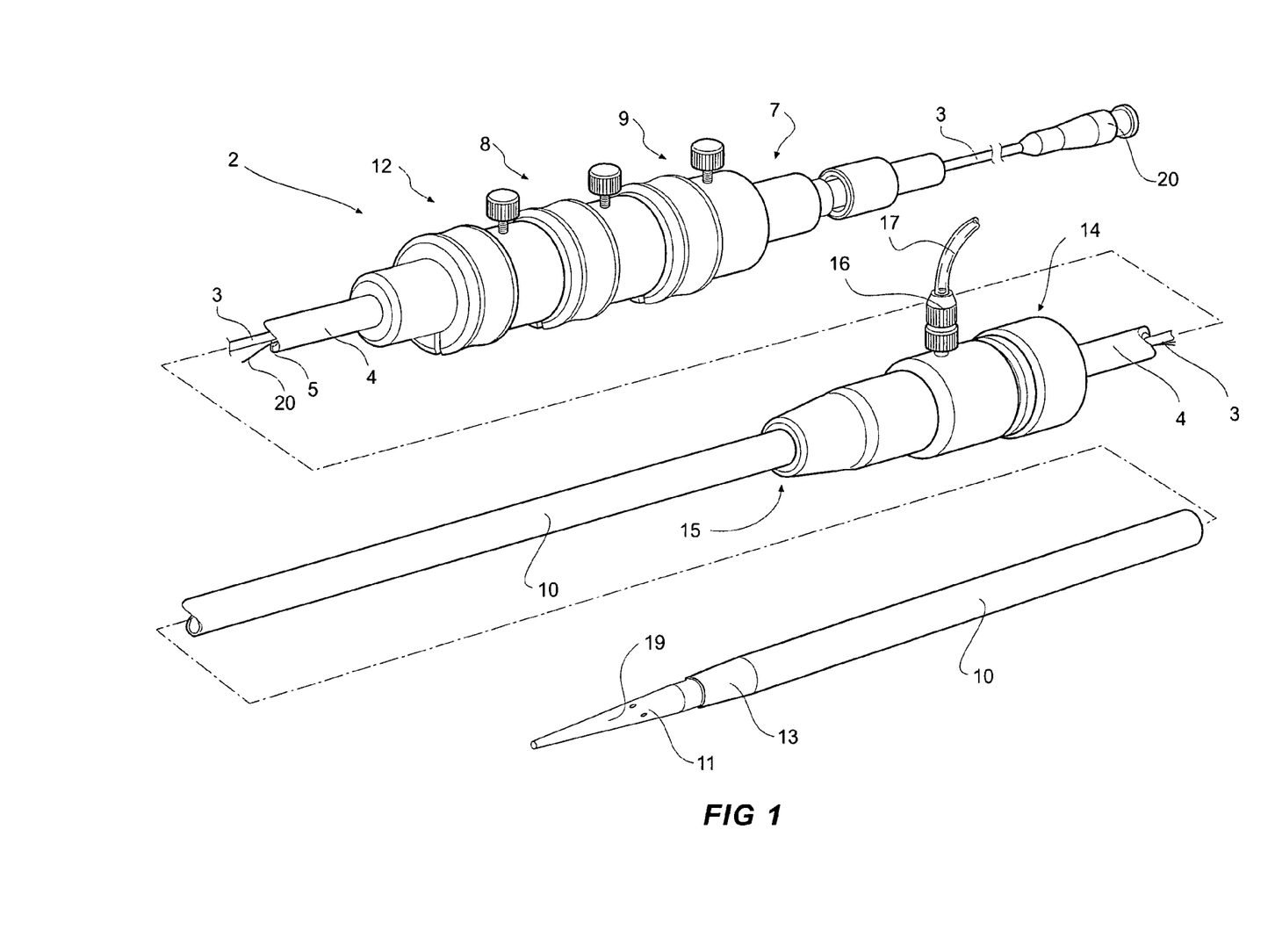
FIG. 1 depicts a introducer or delivery device according to one embodiment of the present invention.
Figure 2:
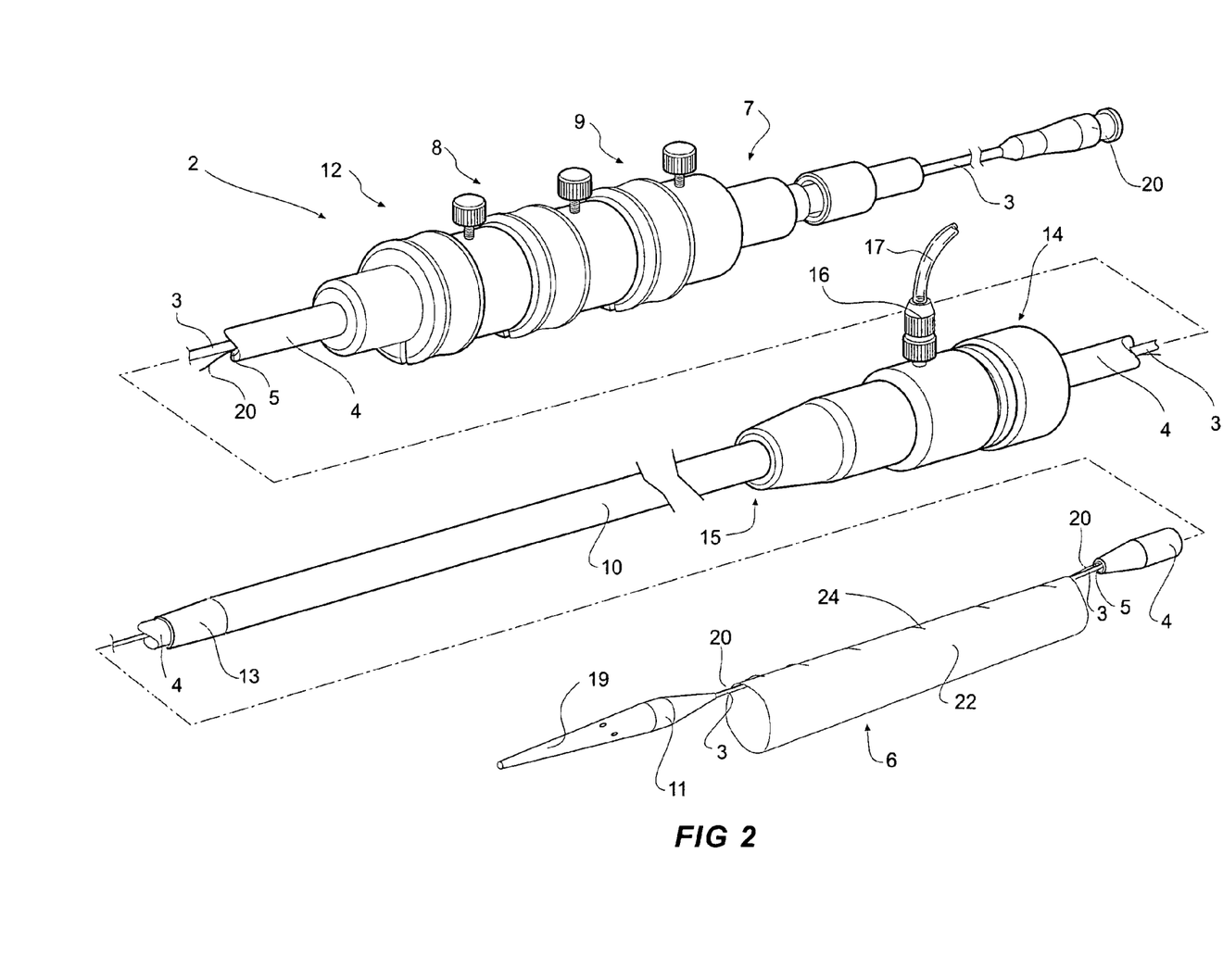
FIG. 2 depicts the introducer or delivery device of FIG. 1 with the sheath withdrawn to show the components underneath it.
Figure 3A:
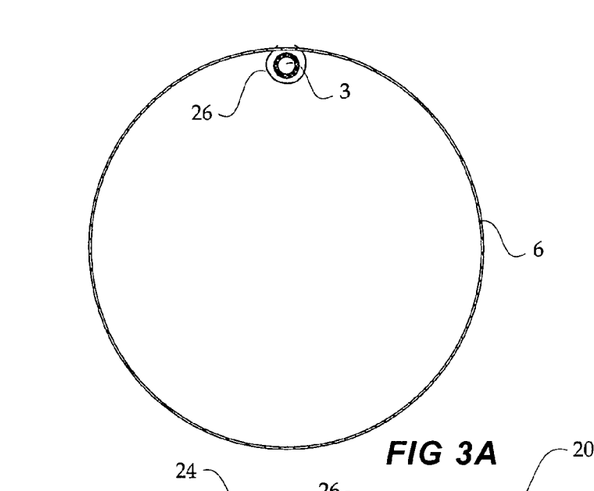
FIGS. 3A and 3B show transverse and longitudinal cross sectional views of a stent graft mounted onto a guide wire catheter of a deployment device according to one embodiment of the present invention.
Figure 3B:
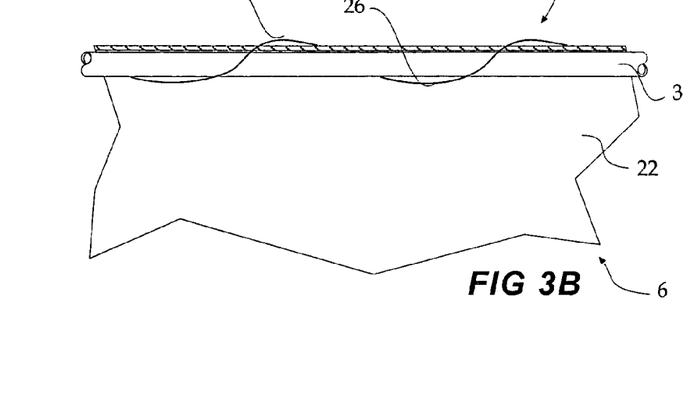

The wire guide is inserted in the vessel with an introducer needle using, for example, the well-known percutaneous vascular access Seldinger technique. A well-known male Luer lock connector hub 20 is attached at the distal end of the guide wire catheter 3 for connection to syringes and other medical apparatus. The handle 7 at the distal end of the pusher catheter 4 remains outside a patient in use and carries the trigger wire release handle mechanisms 8, 9 and 12 used to release the various portions of the stent graft. The proximal end the stent graft 6 is retained on the delivery device by the use of trigger wires (not shown) connected to the release handle 9, the distal end of the stent graft is retained on the delivery device by the use of trigger wires (not shown) connected to the release handle 8. The handle also includes a release mechanism 12 for a release wire for the longitudinal portion of the stent graft according to the present invention as is discussed below.

The stent graft 6 comprises a tubular body 22 of a biocompatible material and a plurality of self expanding stents (not shown for clarity).

A release wire 20 extends from the release mechanism 12 on the handle 7 through the lumen 5 in the delivery catheter 4 and exits at the proximal end of the delivery catheter 4 as shown in FIG. 2. The release wire 20 is then wound around the guide wire catheter 3 and through the material of the tubular body 22 in a spiral fashion so that there are lengths 24 of release wire 20 outside the tubular body and, as can be particularly seen in FIGS. 3A and 3B and FIG. 5, turns 26 of release wire 20 around the guide wire catheter 3. This arrangement holds the guide wire catheter 3 against a selected longitudinal portion of the stent graft. When the stent graft is deployed into the vasculature of a patient and the device is deployed into a curved vessel the guide wire catheter of the deployment device will normally take up a position in the greater radius side of the curve owing to its relative rigidity. Hence the longitudinal portion of the stent graft which is releasably bound to the guide wire catheter will also take up a position at the greater radius side of the curve. This means that a stent graft with a fenestration or scallop which is to be deployed on the greater radius side of the curve can be mounted onto the deployment device with the fenestration or scallop adjacent the guide wire and once deployed the scallop or fenestration will be easier to correctly position. When it is desired to release the stent graft the release wire 20 can be withdrawn by removal of the release wire mechanism 12 which will release the stent graft from its engagement with the guide wire catheter.

In this embodiment the order of placement of the release handle mechanisms 8, 9 and 12 on the handle of the introducer is such that the order of release is the proximal end of the stent graft, the distal end of the stent graft and then the longitudinal portion. In other embodiments and assemblies the order of placement may be different. For instance it may be desirable to release the proximal end, the longitudinal portion and then the distal end.

Figure 4A:
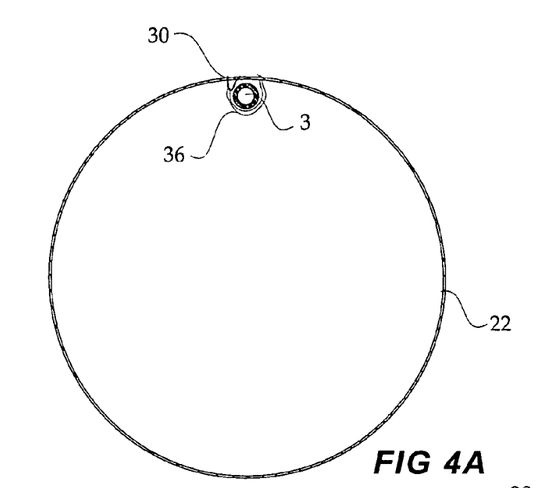
FIGS. 4A and 4B show transverse and longitudinal cross sectional views of a stent graft mounted onto a guide wire catheter of a deployment device according to an alternative embodiment of the present invention.
Figure 4B:
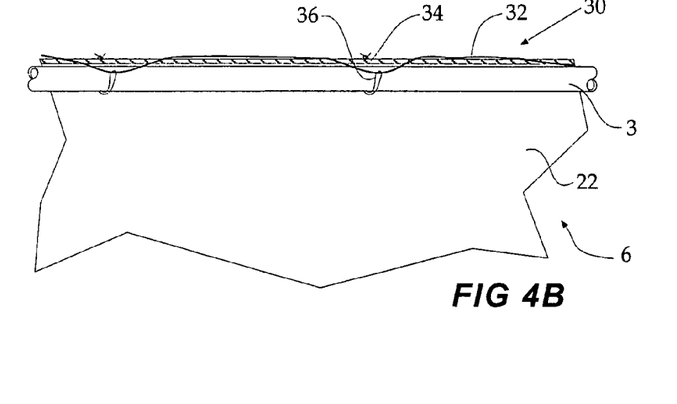
Figure 6:
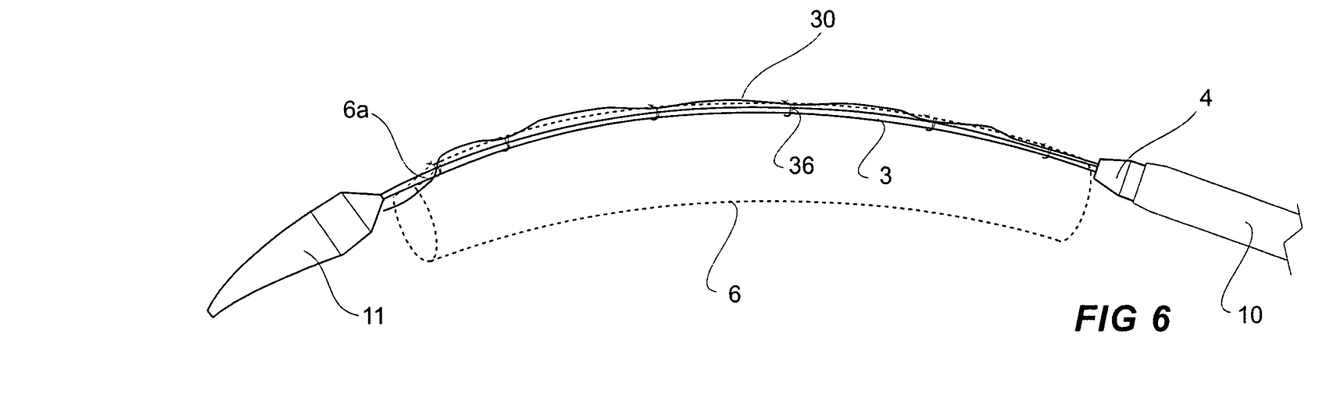
FIG. 6 shows a perspective view of the embodiment shown in FIGS. 4A and 4B.

An alternative embodiment is shown in FIGS. 4A and 4B and FIG. 6. In this embodiment the release wire 30 is stitched through the material of the tubular body 22 along the longitudinal portion of the stent graft which is to be placed into a curved vessel at the greater radius side of the curve. This leaves portions 32 of the release wire 20 outside of the tubular body 22 and loops 34 of the release wire 20 inside the tubular body 22. Loops of biocompatible thread 36 such as suture material are then sewn into the graft material to pass around the guide wire catheter 3 and around the trigger wire loops 34. This arrangement holds the guide wire catheter against a selected longitudinal portion of the stent graft. When the stent graft is deployed into the vasculature of a patient and the device is deployed into a curved vessel the guide wire catheter of the deployment device will normally take up a position in the greater radius side of the curve and hence the longitudinal portion of the stent graft which is releasably bound to the guide wire catheter will also take up a position at the greater radius side of the curve. This means that a stent graft with a fenestration or scallop which is to be deployed on the greater radius side of the curve can be mounted onto the deployment device with the fenestration or scallop adjacent the guide wire and once deployed the scallop or fenestration will be easier to correctly position. When it is desired to release the stent graft the release wire 30 can be withdrawn which will release each of the loops 36 and hence the stent graft from its engagement with the guide wire catheter. The loops 36 remain sewn into the wall of the graft material and will not cause a problem in the blood stream.

Figure 5:
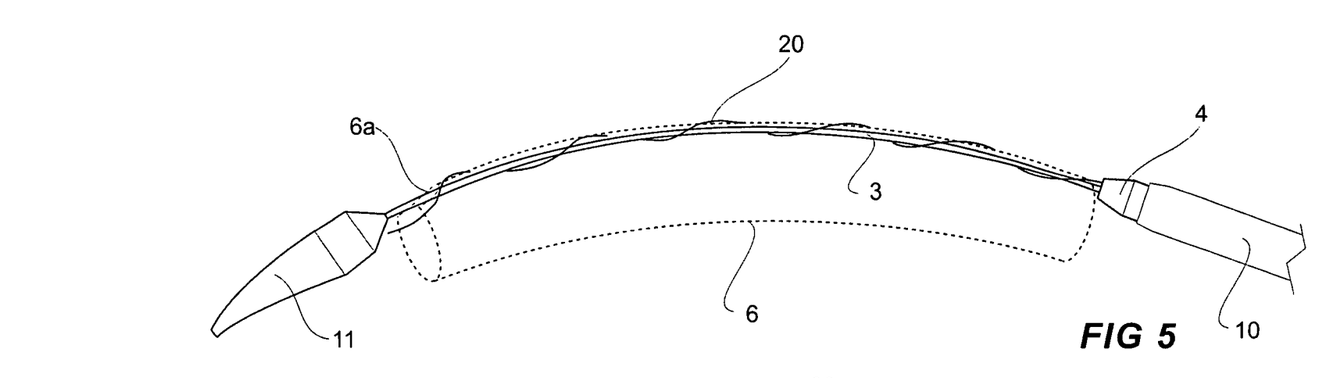
FIG. 5 shows a perspective view of the embodiment shown in FIGS. 3A and 3B.

FIGS. 5 and 6 show the alternative embodiments of the invention when a guide wire catheter is curved such as when it is placed into a curved vessel such as the thoracic of a patient. It will be noted that the stent graft 6 when not constrained by the sheath 10 has a longitudinal portion retained against the guide wire catheter 3 and otherwise extends out to one side of the guide wire catheter. The stent graft has a scallop 6a at its proximal end and the scallop is aligned with the guide wire catheter. When the guide wire catheter 3 is bent the longitudinal portion of the stent graft with a scallop 6a is deployed on the greater radius side of the curve.

If by suitable imaging techniques the great vessel such as the left subclavian artery is seen to be off centre at the top of the curve of the thoracic arch then the stent graft can be mounted onto the deployment device with its scallop similarly off centre from the longitudinal portion aligned with the guide wire catheter of the deployment device.

Figure 7:
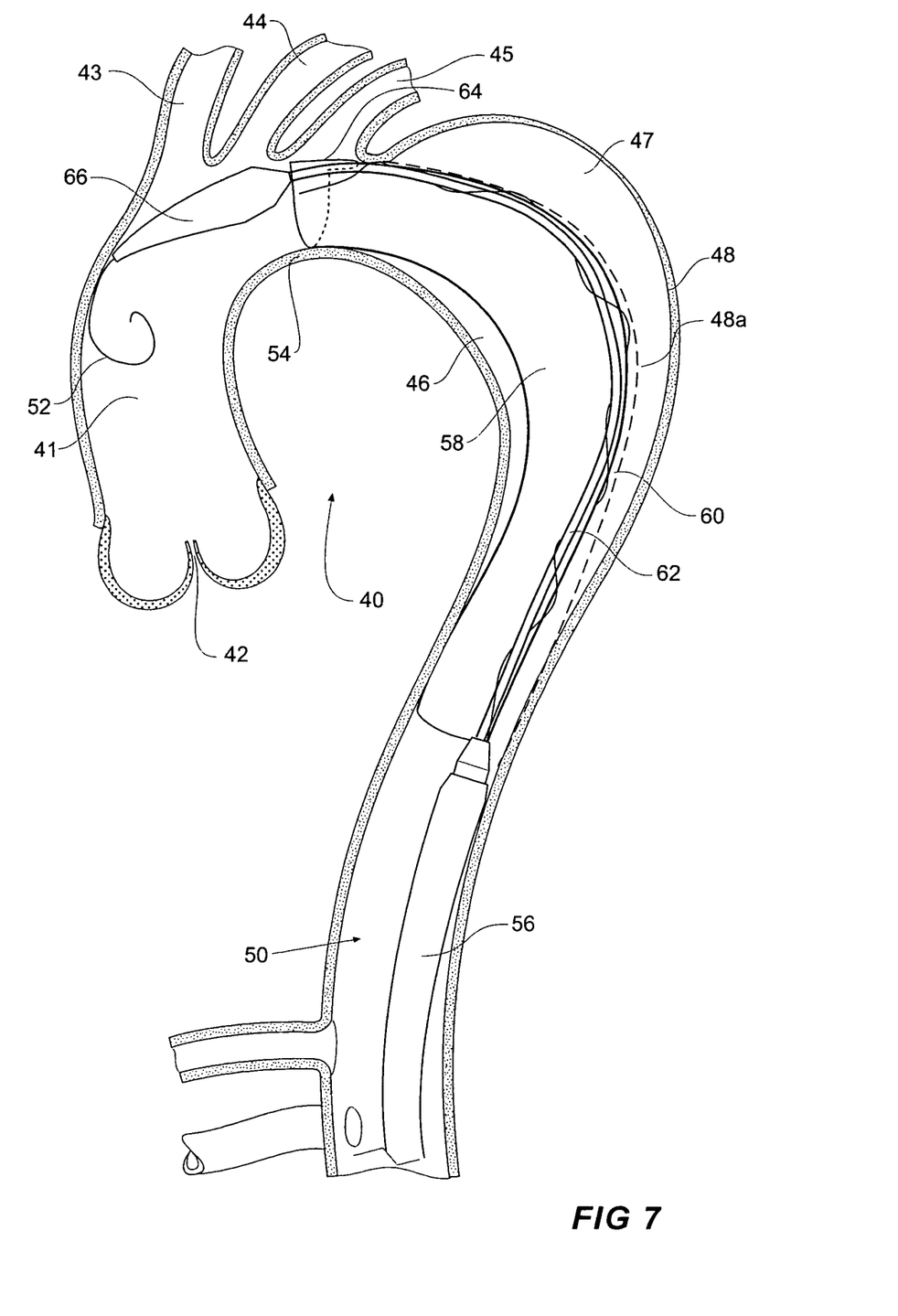
FIG. 7 shows a schematic view of an aorta of a patient with a deployment device and stent graft according to the present invention deployed therein.

FIG. 7 shows a cross sectional view of a thoracic aorta. It will be seen that the thoracic aorta 40 comprises an ascending aorta 41 which receives blood from the heart though an aortic valve 42. At the upper end of the ascending aorta there are branches for the great vessels, the innominate artery 43, the left common carotid artery 44 and the left subclavian artery 45. The aorta after these great vessels is referred to as the descending aorta 46 and it is in this region that a thoracic aortic aneurysm 47 can occur. In a thoracic aortic aneurysm part of the wall 48 of the descending aorta swells and can burst with serious consequences. The dotted line 48a shows what would be the normal curved wall of the descending aorta.

As shown in FIG. 7 a deployment device 50 has been deployed up through the descending aorta over a guide wire 52. The proximal end of the deployment device extends over the thoracic arch 54 and into the ascending aorta 41. The sheath 56 has been withdrawn to partially release the stent graft 58 but it is still retained by the release wire 60 onto the guide wire catheter 62 of the deployment device 50. The release wire 60 is wound in a spiral fashion around the guide wire catheter 62 and through the material of the stent graft 58. It will be noted that as the thoracic arch is curved the guide wire catheter of the deployment device has taken up a position on the greater radius side of the curve and hence the longitudinal portion of the stent graft which is releasably bound to the guide wire catheter has also take up a position at the greater radius side of the curve. This enables the scallop 64 at the proximal end of the stent graft 58, which is positioned adjacent the guide wire catheter 3, to be adjacent the left subclavian artery 45 so that the stent graft does not occlude that artery. At the stage shown both the proximal and distal ends of the stent graft have been release but as discussed earlier the distal end may be retained and not released until the longitudinal portion retention according to the present invention has been released.

Withdrawal if the release wire 60 by removal of the release handle mechanism 12 (see FIG. 1) enables the nose cone dilator 66 to be retracted to the sheath 56 and the entire deployment device can be withdrawn.

Figure 8:
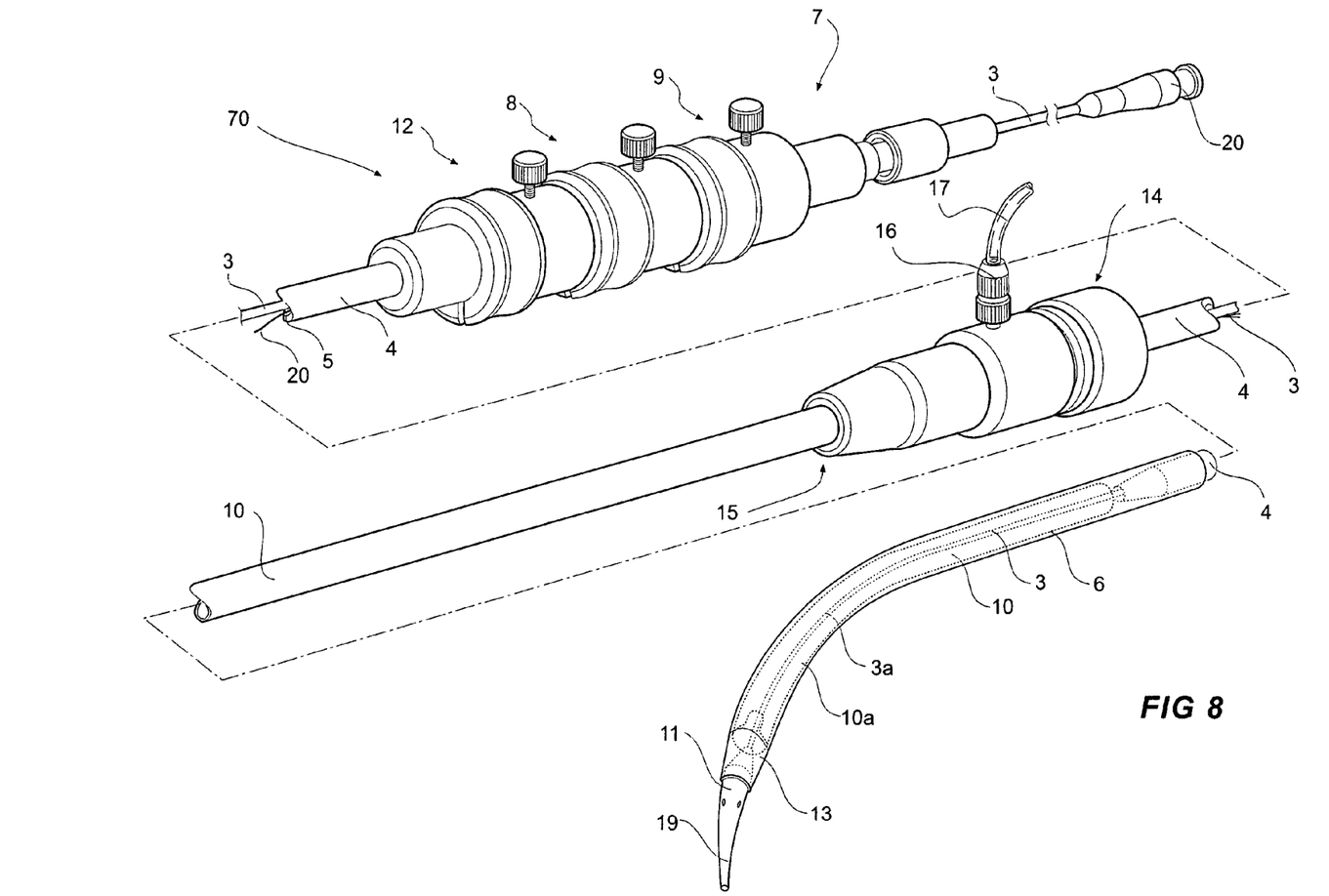
FIG. 8 shows an alternative embodiment of introducer or delivery device according to the present invention.
Figure 9:
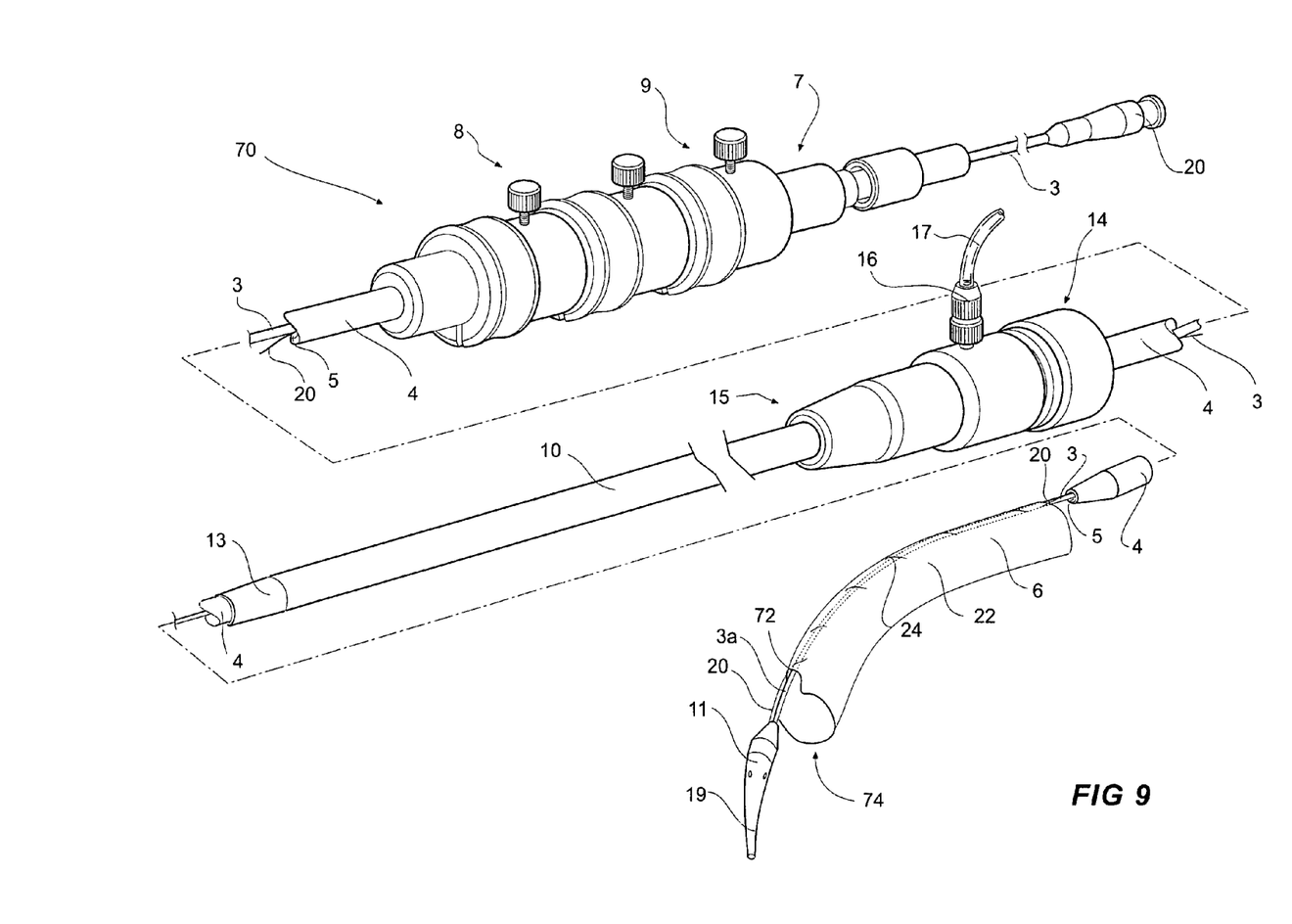
FIG. 9 shows the embodiment of FIG. 8 with the sheath withdrawn to show the components underneath it.

FIGS. 8 and 9 show an alternative embodiment of the present invention. The embodiment is similar to that shown in FIG. 1 and the same reference numerals are used for corresponding items.

The deployment device 70 has a guide wire catheter 3 which extends from a distal handle 7 to a proximal tapered nose cone dilator 11 longitudinally through a passageway or lumen 5 of a delivery catheter 4 which is connected to the handle 7 at its distal end. An introducer sheath 10 fits coaxially around the delivery catheter 4 and extends from a tapered proximal end 13 which optionally includes a radiopaque marker to a connector valve and manipulator 14 attached about distal end 15 of the sheath. The introducer sheath 10 extends proximally to the nose cone dilator 11 and covers the stent graft 6 during introduction of the deployment device into a patient and is withdrawn distally to expose the stent graft 6 during deployment when the deployment device is in a selected position within the vasculature of a patient.

The sheath in this embodiment is flexible but has a preformed curve 10a towards its proximal end so that the delivery device can more easily conform to the shape of the thoracic arch without putting an unacceptable stress against the wall of the thoracic arch. The preformed curved portion of the introducer sheath 10 is sufficiently flexible, however, that when it is retracted back to the pusher catheter 4 as shown in FIG. 9 the curved portion 10a of the introducer sheath 10 straightens out.

The guide wire catheter 3 also has a preformed curve 3a just distal of the nose cone dilator 11 again so that the delivery device can more easily conform to the shape of the thoracic arch without putting an unacceptable stress against the wall of the thoracic arch.

The stent graft or implantable device 6 is carried on the guide wire catheter 3 proximally of the delivery catheter 4 and distally of the nose cone dilator 11. The stent graft 6 is not shown in FIG. 8 but can be seen in FIG. 9 in which the sheath 10 is shown retracted to the pusher catheter 4. The stent graft 6 comprises a tubular body 22 of a biocompatible material and a plurality of self expanding stents (not shown for clarity). In this embodiment the stent graft has a scallop 72 at its proximal end 74. When correctly deployed the scallop will allow access to the left subclavian artery from the thoracic arc while still allowing a sufficient sealing region or landing zone between the thoracic arch and the aneurysm.

Connector valve 14 includes a silicone disk (not shown) for preventing the backflow of fluids therethrough. The disk includes a slit for the insertion of the nose cone dilator 11 and delivery catheter 4. Connector 14 also includes side arm 16 to which a tube 17 is connected for introducing and aspirating fluids therethrough. Nose cone dilator 11 includes a tapered proximal end 19 for accessing and dilating a vascular access site over a well-known and commercially available wire guide (not shown).

To deploy the stent graft a wire guide is inserted in the vessel with an introducer needle using, for example, the well-known percutaneous vascular access Seldinger technique. A well-known male Luer lock connector hub 20 is attached at the distal end of the guide wire catheter 3 for connection to syringes and other medical apparatus. The handle 7 at the distal end of the pusher catheter 4 remains outside a patient in use and carries the trigger wire release handle mechanisms 8, 9 and 12 used to release the various portions of the stent graft. The proximal end the stent graft 6 is retained on the delivery device by the use of trigger wires (not shown) connected to the release handle 9, the distal end of the stent graft is retained on the delivery device by the use of trigger wires (not shown) connected to the release handle 8. The handle also includes a release mechanism 12 for a release wire for the longitudinal portion of the stent graft according to the present invention as is discussed below.

A release wire 20 extends from the release mechanism 12 on the handle 7 through the lumen 5 in the delivery catheter 4 and exits at the proximal end of the delivery catheter 4 as shown in FIG. 2. The release wire 20 is then wound around the guide wire catheter 3 and through the material of the tubular body 22 in a spiral fashion so that there are lengths 24 of release wire 20 outside the tubular body and turns 26 of release wire 20 around the guide wire catheter 3. This arrangement holds the guide wire catheter 3 against a selected longitudinal portion of the stent graft. When the stent graft is deployed into the vasculature of a patient and the device is deployed into a curved vessel the curved guide wire catheter 3a of the deployment device will take up a position in the greater radius side of the curve. Hence the longitudinal portion of the stent graft which is releasably bound to the guide wire catheter will also take up a position at the greater radius side of the curve. This means that a stent graft with a fenestration or scallop which is to be deployed on the greater radius side of the curve can be mounted onto the deployment device with the fenestration or scallop adjacent the guide wire and once deployed the scallop or fenestration will be easier to correctly position. When it is desired to release the stent graft the release wire 20 can be withdrawn by removal of the release wire mechanism 12 which will release the stent graft from its engagement with the guide wire catheter.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft delivery system in which a stent graft comprising a substantially tubular body is retained on the delivery system, comprising a guide wire catheter and a releasable fastening device extending the length of the stent graft between the stent graft and the delivery system whereby the stent graft is releasably retained on the delivery device to bend therewith, the releasable fastening device comprising a release wire wound around the guide wire catheter at least partially within the substantially tubular body and through the material of the stent graft in a spiral manner along the length of the stent graft.

2. A stent graft delivery system according to claim 1, further including a flexible sheath over a pusher catheter and extending to a nose cone dilator for retaining the stent graft in a contracted configuration on the guide wire catheter.

3. An endovascular delivery assembly including a delivery device and a stent graft comprising a substantially tubular body mounted thereon; the delivery device comprising a pusher catheter, a distal handle on the pusher catheter, a proximal nose cone dilator, a guide wire catheter extending from the pusher catheter to and into the nose cone dilator and a flexible sheath over the pusher catheter and extending to the nose cone dilator and thereby retaining the stent graft in a contracted conformation on the guide wire catheter; the stent graft comprising a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and the guide wire catheter passing through the lumen of the stent graft; the assembly including a release wire system for releasably retaining the stent graft to the guide wire catheter, the release wire system including a release wire wound around the guide wire catheter at least partially within the substantially tubular body and through the material of the stent graft in a spiral manner along the length of the stent graft and the release wire extending to a release mechanism on the distal handle to enable withdrawal of the release wire whereby the stent graft is temporarily affixed to the guide wire catheter and curves with curvature of the guide wire catheter in use and whereby when the release wire is withdrawn the stent graft is released from the guide wire catheter.

4. An endovascular delivery assembly according to claim 3 wherein the pusher catheter comprises a longitudinal lumen therethrough, the guide wire catheter extending through the longitudinal lumen so as to be movable longitudinally and rotationally with respect to the pusher catheter.

5. An endovascular delivery assembly according to claim 3, wherein the release wire extends to a release mechanism on the distal handle to enable withdrawal of the release wire.

6. An endovascular delivery assembly according to claim 3, wherein the spiral wound wire comprises a pitch of between 20 to 40 mm.

7. An endovascular delivery assembly according to claim 3, comprising a releasable retention system for a proximal end of the stent graft.

8. An endovascular delivery assembly according to claim 3, comprising a releasable retention system for a distal end of the stent graft.

9. An endovascular delivery assembly according to claim 3, wherein the guide wire catheter has a pre-formed curve just distal of the nose cone dilator.

10. An endovascular delivery assembly according to claim 3, wherein the flexible sheath of the delivery device has a pre-formed curve at its proximal end.

11. A stent graft delivery system in which a stent graft comprising a substantially tubular body is retained on the delivery system, comprising a guide wire catheter and a releasable fastening device extending the length of the stent graft between the stent graft and the delivery system whereby the stent graft is releasably retained on the delivery device to bend therewith, the releasable fastening device comprising a release wire stitched along the length of the stent graft and a plurality of suture loops fastened to the tubular body of the stent graft and passed around the guide wire catheter at least partially within the substantially tubular body and around the stitches of the release wire.

12. A stent graft delivery system according to claim 11, further including a flexible sheath over a pusher catheter and extending to a nose cone dilator for retaining the stent graft in a contracted configuration on the guide wire catheter.

13. An endovascular delivery assembly according to claim 12, wherein the flexible sheath of the delivery device has a pre-formed curve at its proximal end.

14. An endovascular delivery assembly including a delivery device and a stent graft comprising a substantially tubular body mounted thereon; the delivery device comprising a pusher catheter, a distal handle on the pusher catheter, a proximal nose cone dilator, a guide wire catheter extending from the pusher catheter to and into the nose cone dilator and a flexible sheath over the pusher catheter and extending to the nose cone dilator and thereby retaining the stent graft in a contracted conformation on the guide wire catheter; the stent graft comprising a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and the guide wire catheter passing through the lumen of the stent graft; a release wire system to releasably retain the stent graft to the guide wire catheter, the release wire system including a release wire stitched along the length of the stent graft and a plurality of suture loops fastened to the tubular body of the stent graft and looped around the guide wire catheter at least partially within the substantially tubular body and the stitches of the release wire and the release wire extending to a release mechanism on the distal handle to enable withdrawal of the release wire whereby the stent graft is temporarily affixed to the guide wire catheter and curves with curvature of the guide wire catheter in use and whereby when the release wire is withdrawn the stent graft is released from the guide wire catheter.

15. An endovascular delivery assembly according to claim 14, wherein the pusher catheter comprises a longitudinal lumen therethrough, the guide wire catheter extending through the longitudinal lumen so as to be movable longitudinally and rotationally with respect to the pusher catheter.

16. An endovascular delivery assembly according to claim 14, wherein the release wire extends to a release mechanism on the distal handle to enable withdrawal of the release wire.

17. An endovascular delivery assembly according to claim 14, comprising a releasable retention system for a proximal end of the stent graft.

18. An endovascular delivery assembly according to claim 14, comprising a releasable retention system for a distal end of the stent graft.

19. An endovascular delivery assembly according to claim 14, wherein the guide wire catheter has a pre-formed curve just distal of the nose cone dilator.

* * * * *